(12) United States Patent
Okada

(10) Patent No.: US 12,274,608 B2
(45) Date of Patent: Apr. 15, 2025

(54) DISPOSABLE DIAPER WITH IMPROVED ABSORPTION AND LEAKAGE PROTECTION

(71) Applicant: DAIO PAPER CORPORATION, Ehime (JP)

(72) Inventor: Yuki Okada, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 392 days.

(21) Appl. No.: 17/771,620

(22) PCT Filed: Nov. 18, 2020

(86) PCT No.: PCT/JP2020/043056
§ 371 (c)(1),
(2) Date: Apr. 25, 2022

(87) PCT Pub. No.: WO2021/100777
PCT Pub. Date: May 27, 2021

(65) Prior Publication Data
US 2022/0409448 A1    Dec. 29, 2022

(30) Foreign Application Priority Data

Nov. 20, 2019  (JP) .................. 2019-209788

(51) Int. Cl.
*A61F 13/512*  (2006.01)
*A61F 13/49*   (2006.01)
*A61F 13/511*  (2006.01)

(52) U.S. Cl.
CPC .......... *A61F 13/5126* (2013.01); *A61F 13/49* (2013.01); *A61F 2013/51117* (2013.01); *A61F 2013/5127* (2013.01)

(58) Field of Classification Search
None
See application file for complete search history.

(56) References Cited

U.S. PATENT DOCUMENTS

2004/0122396 A1 * 6/2004 Maldonado ............... B32B 3/28
                                                    604/383
2016/0129626 A1    5/2016 Arora et al.

FOREIGN PATENT DOCUMENTS

| CN | 107072835 | 8/2017 | |
| EP | 1371379 A1 * | 12/2003 | ........... A61F 13/511 |
| JP | 2013-066598 | 4/2013 | |
| JP | 2018-102836 | 7/2018 | |
| JP | 2019-162303 | 9/2019 | |
| JP | 2019-171023 | 10/2019 | |

OTHER PUBLICATIONS

International Search Report for PCT/JP2020/043056, dated Jan. 26, 2021.

* cited by examiner

*Primary Examiner* — Michele Kidwell
(74) *Attorney, Agent, or Firm* — Andrus Intellectual Property Law, LLP

(57) ABSTRACT

A disposable diaper capable of providing good suppression of diaper rash. A disposable diaper including top sheet 30 constituting a surface for use, liquid-impervious sheet provided on the under face side, and absorbent element interposed therebetween, wherein the top sheet is formed of perforated nonwoven fabric having a number of holes arranged at intervals and each penetrating the two sides of the fabric, and a moisturizer M composed mainly of glycerin is applied to the top sheet.

2 Claims, 9 Drawing Sheets

[FIG.1]
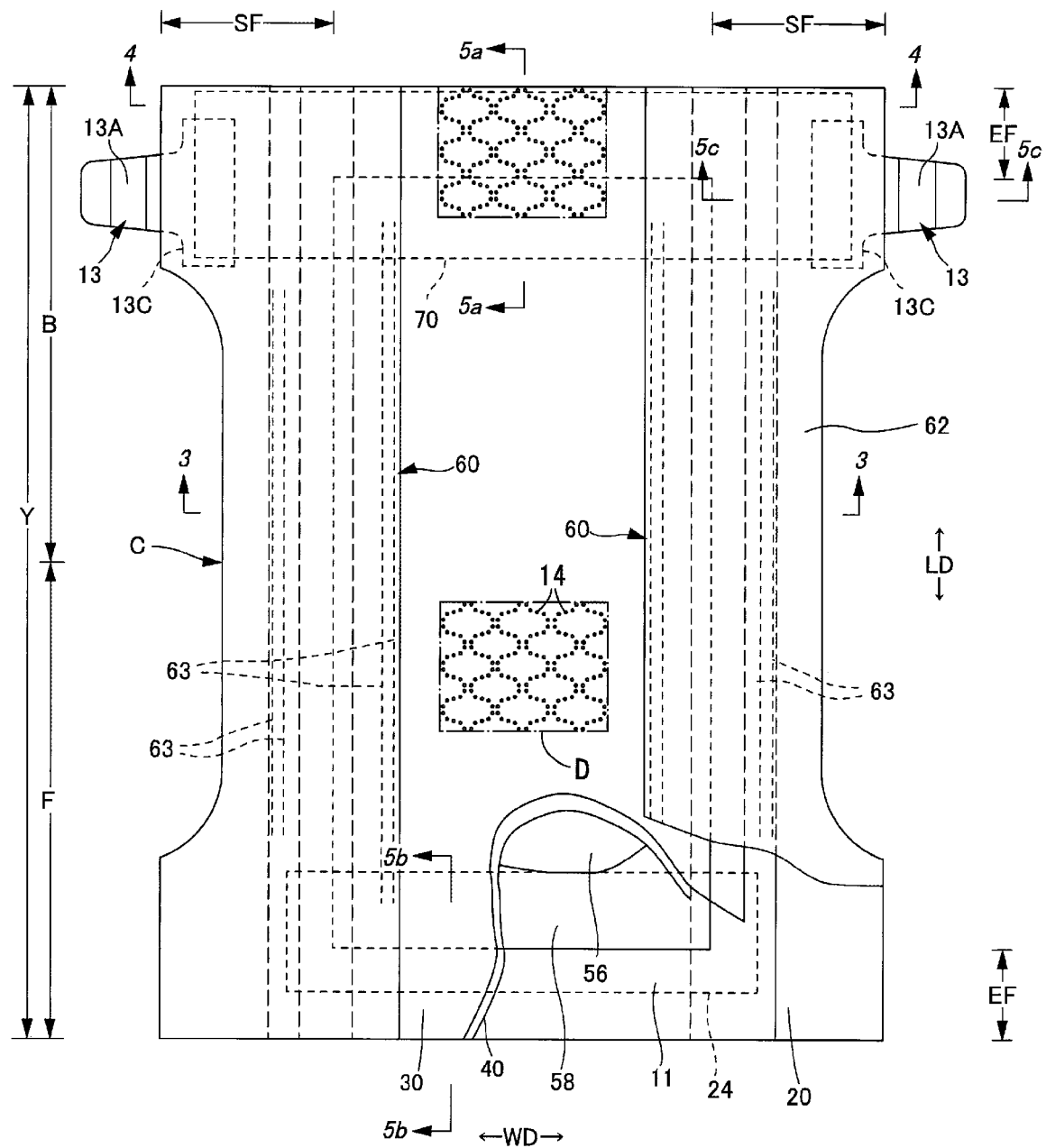

[FIG.2]
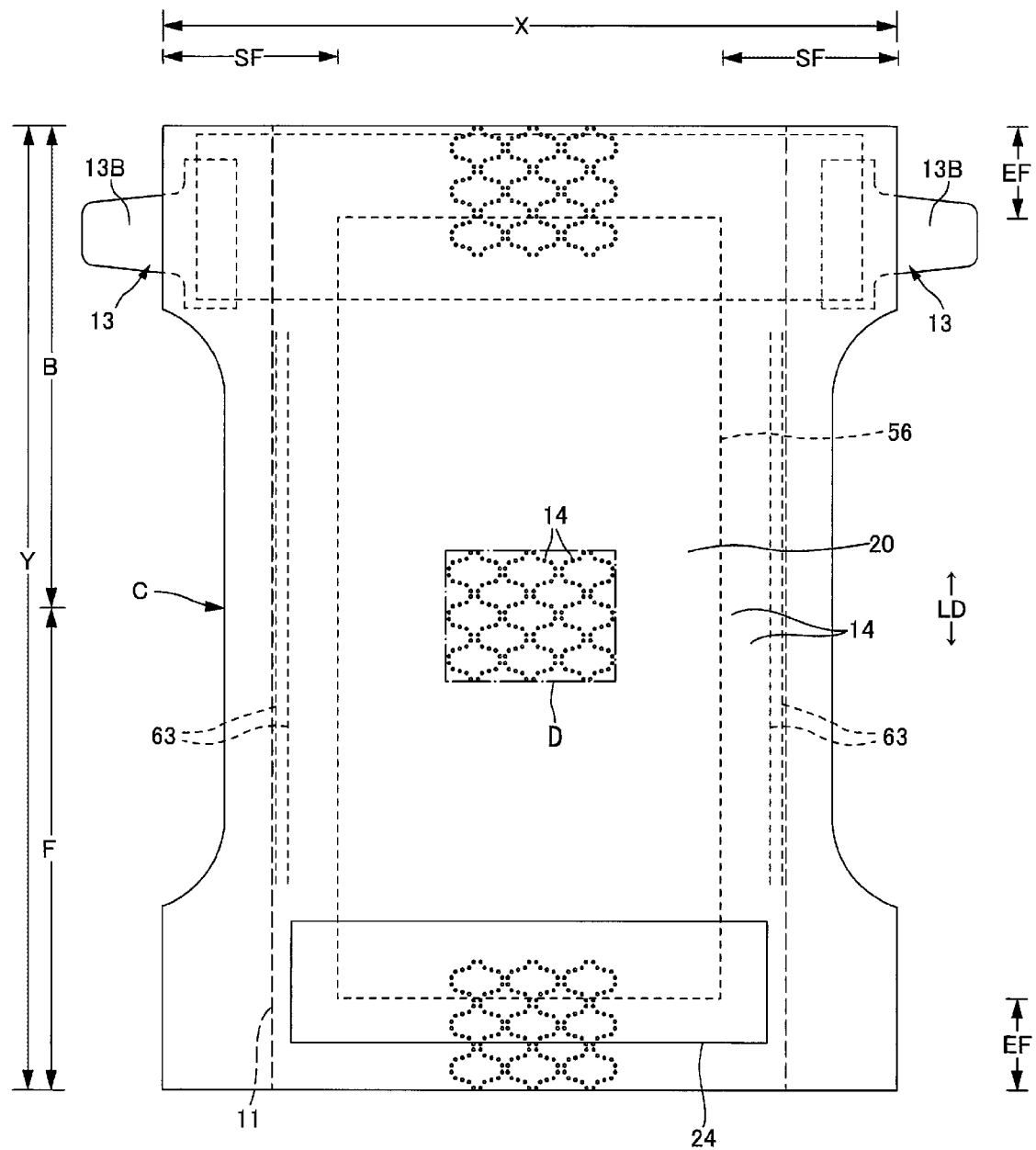

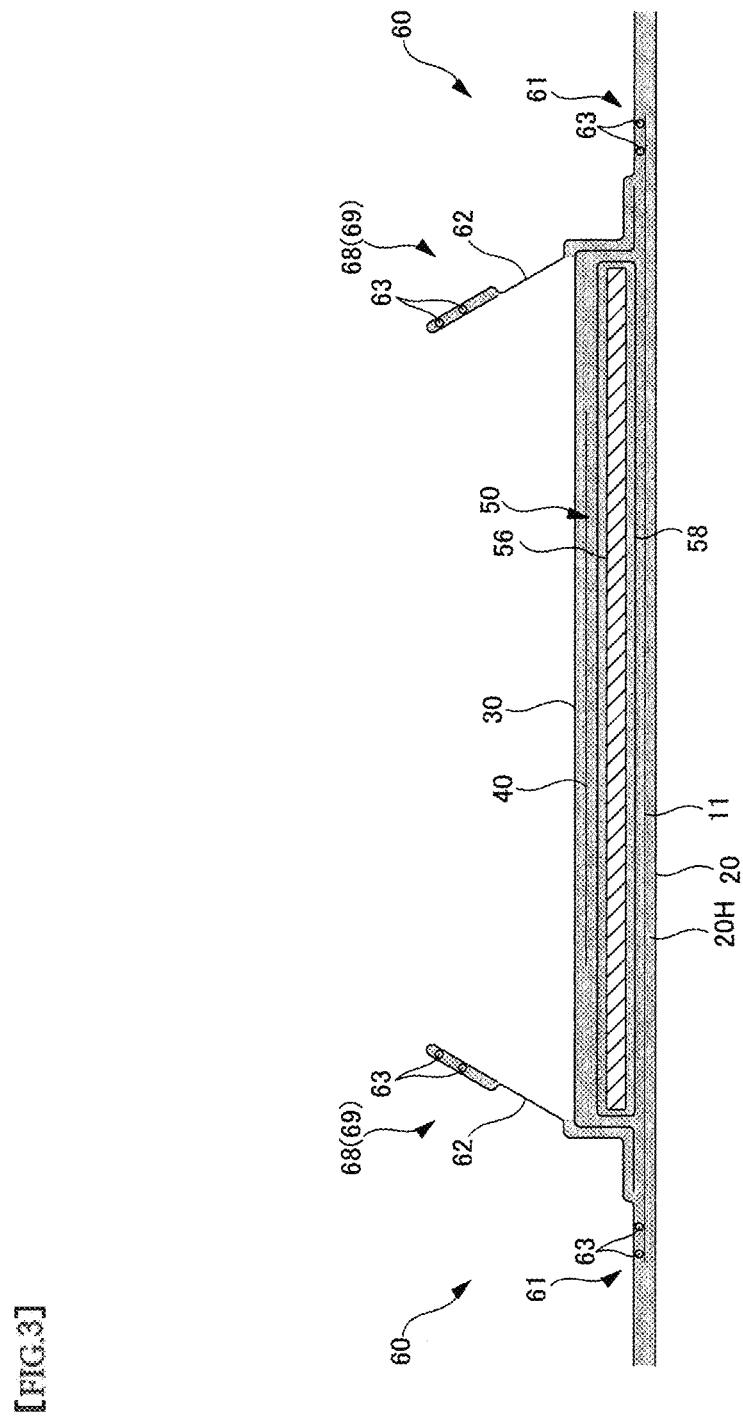

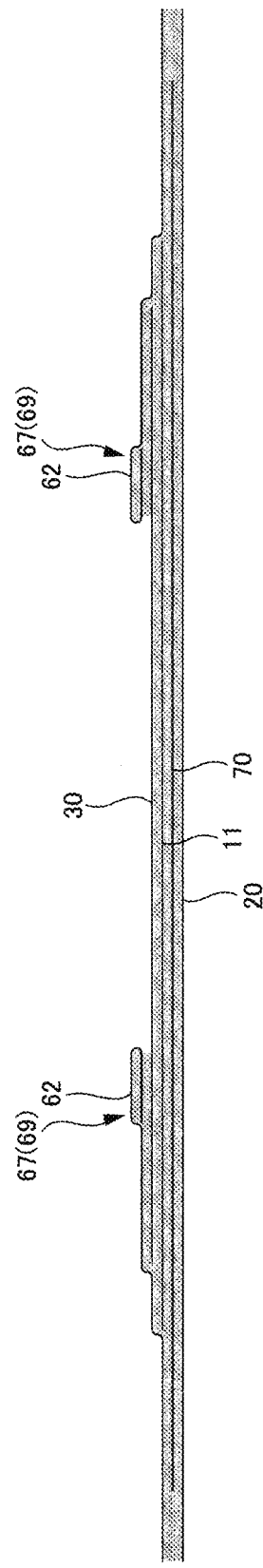

[FIG.5]
(a)
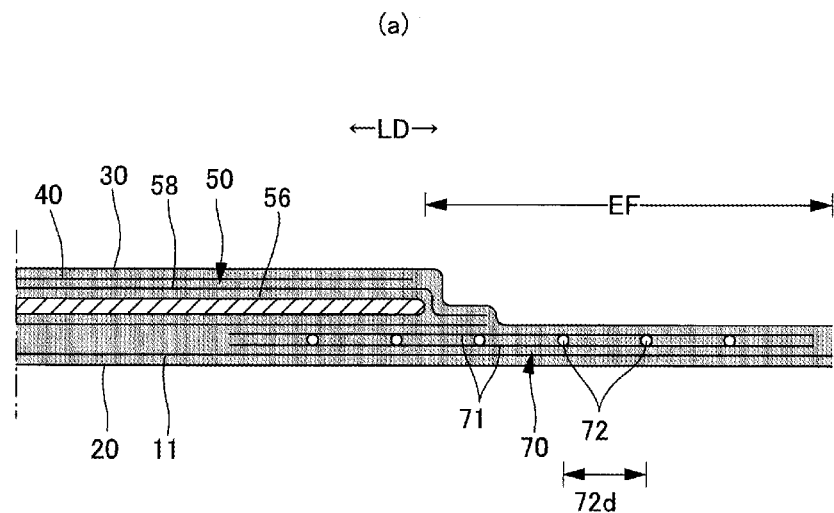
(b)
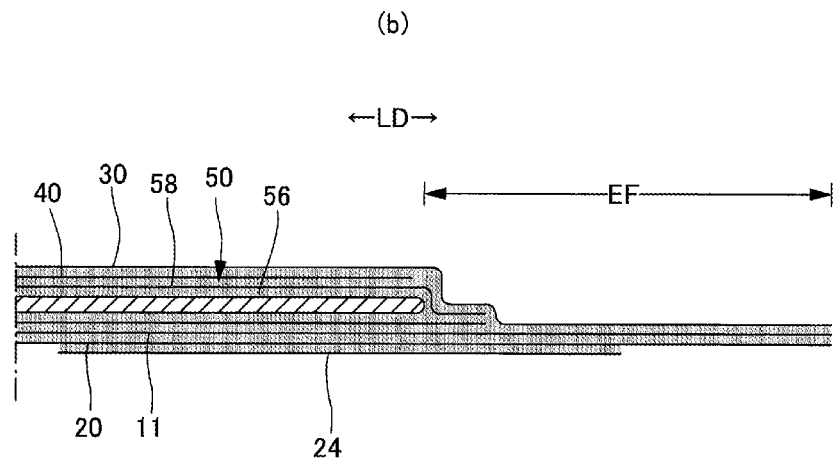
(c)
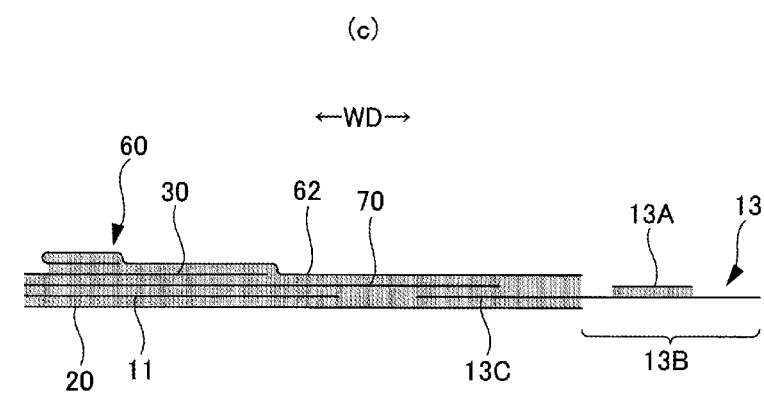

[FIG.6]
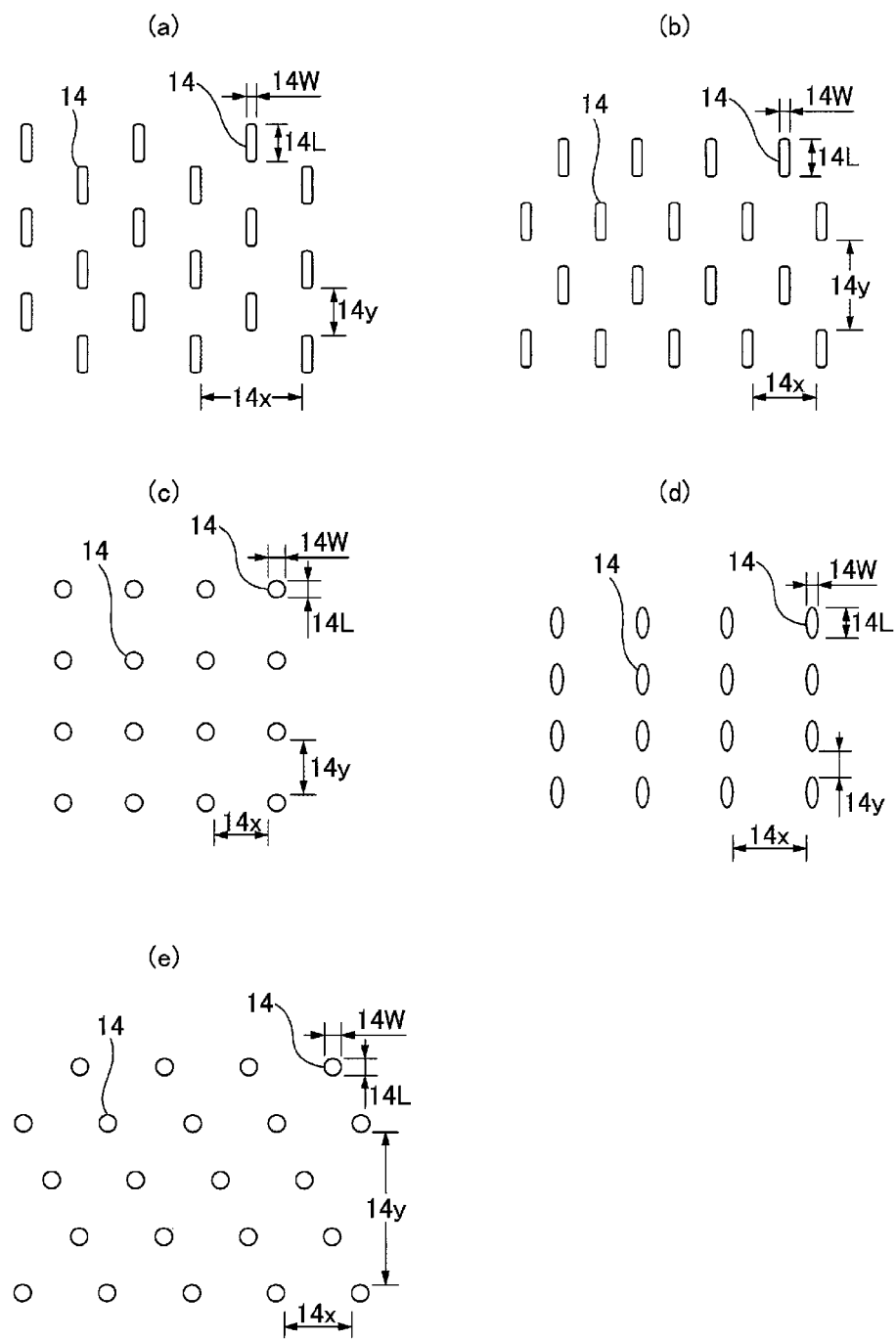

[FIG.7]
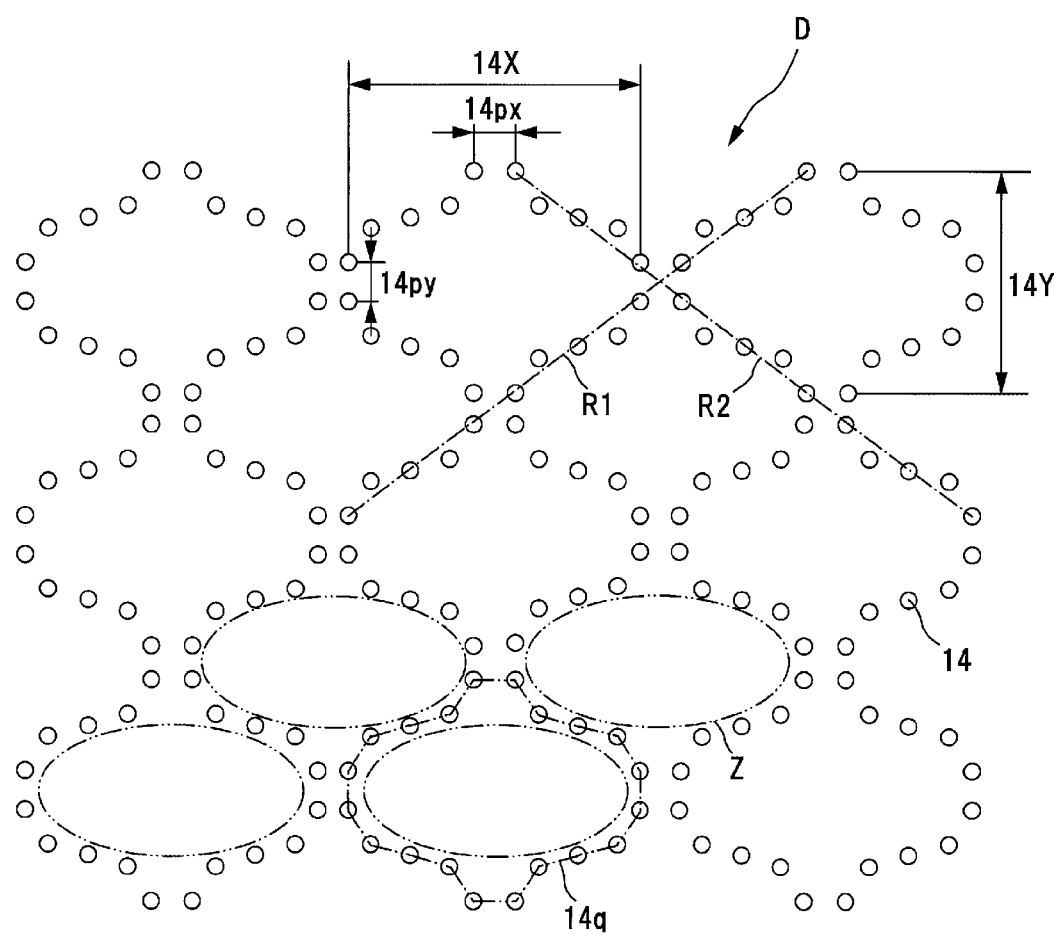

[FIG.8]
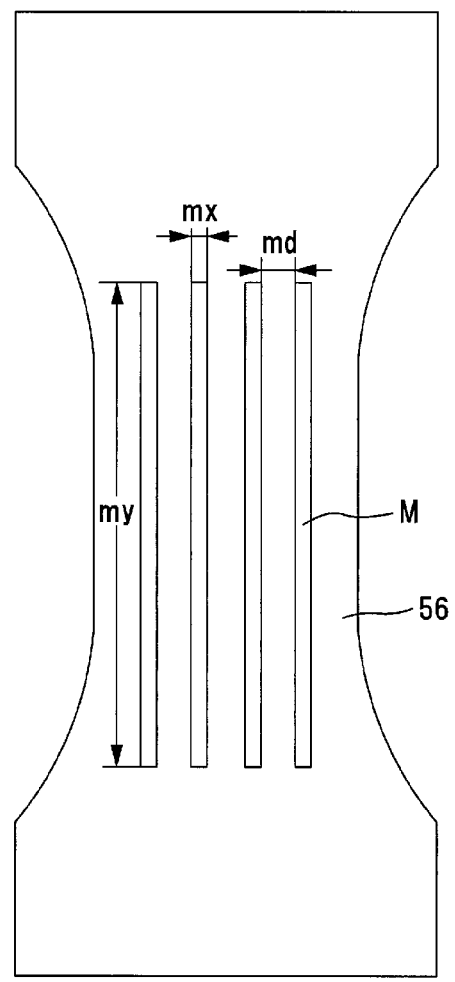

[FIG.9]
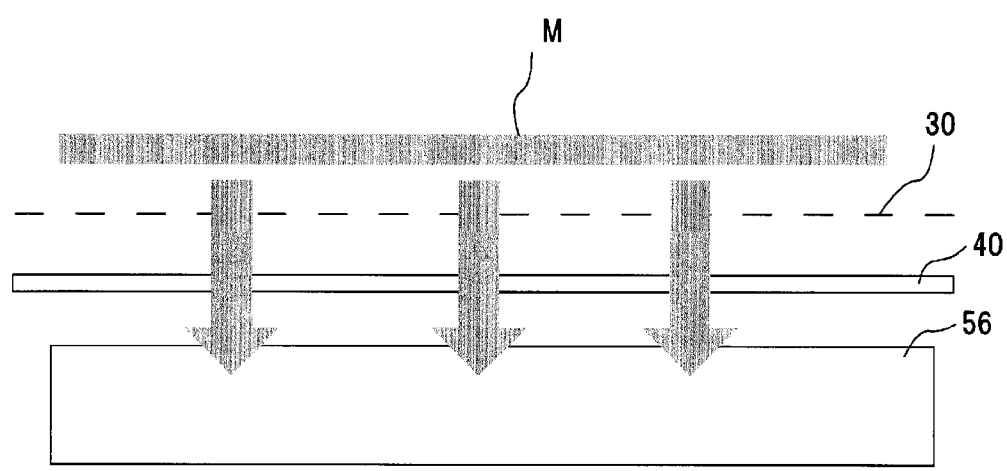

DISPOSABLE DIAPER WITH IMPROVED ABSORPTION AND LEAKAGE PROTECTION

CROSS-REFERENCE TO RELATED APPLICATIONS

This application is the U.S. national stage application of International Application PCT/JP2020/043056, filed Nov. 18, 2020, which international application was published on May 27, 2021, as International Publication WO 2021/100777 in the Japanese language. The International Application claims priority of Japanese Patent Application No. 2019-209788, filed Nov. 20, 2019. The international application and Japanese application are both incorporated herein by reference, in entirety.

TECHNICAL FIELD

The present invention relates to disposable diapers.

BACKGROUND ART

Disposable wearable articles, particularly, disposable diapers, often pose skin problems, in particular, skin rash of wearers.

Such problems may result from friction between the skin and a diaper when worn, or irritation to the skin caused by body fluid or bodily wastes (urine, loose stool) when a diaper is worn over a prolonged period of time.

In particular, irritation to the skin caused by loose stool being in contact with skin for a long period of time is a major factor. This may be avoided by diapers promptly absorbing loose stool into an absorber body. Diapers promptly absorbing loose stool into an absorber body may help not only in reducing skin irritation, but also in preventing leakage through leg portion or back portion of the diaper.

A major factor in obstructing absorption of loose stool through a top sheet is that components of loose stool that are incapable of permeating the top sheet remain on the surface of the fibers constituting the top sheet to cause clogging. A second major factor is that the defecation speed is faster than the absorption rate of diapers, resulting in unabsorbed loose stool components remaining on the top sheet.

Accordingly, it is of crucial importance to cause diapers to promptly absorb loose stool into the absorber body.

Patent Literature 1 discloses to provide a skin care medicine, in particular a skin care medicine made of a diamide derivative, between so-called gather cuffs of a diaper disposed on its widthwise opposite sides.

Baby diapers, in particular, are prone to cause so-called diaper rash as the skin of babies is sensitive.

PRIOR ART LITERATURE

Patent Literature

Patent Literature 1: JP 2018-102836 A

SUMMARY OF THE INVENTION

Problems to be Solved by the Invention

Yet there is a limit on controlling diaper rash by arrangement of the skin care medicine made of a diamide derivative. That is, if loose stool components do not promptly pass the top sheet, it is difficult to control diaper rash by depending only on the skin care medicine.

In view of the above, it is a primary object of the present invention to provide a disposable diaper providing good suppression of diaper rash.

Means for Solving the Problem

Typical aspects of the present invention solving the above problem are as follows.
<Typical Aspect>
A disposable diaper including a top sheet constituting a surface for use, a liquid-impervious sheet provided on an under face side, and an absorbent element interposed therebetween,
  wherein the top sheet is of perforated nonwoven fabric having a number of holes arranged at intervals and each penetrating two sides of the fabric, and
  wherein a moisturizer composed mainly of glycerin is applied to the top sheet.

Effect of the Invention

According to the present invention, advantages such as good suppression of diaper rash may be achieved.

BRIEF DESCRIPTION OF THE DRAWINGS

FIG. 1 is a plan view of a tape-type disposable diaper in its spread state, illustrating the inner surface thereof.

FIG. 2 is a plan view of the tape-type disposable diaper in its spread state, illustrating the outer surface thereof.

FIG. 3 is a cross sectional view taken along lines 3-3 in FIG. 1.

FIG. 4 is a cross sectional view taken along lines 4-4 in FIG. 1.

FIG. 5(a) is a cross sectional view taken along lines 5a-5a in FIG. 1, FIG. 5(b) is a cross sectional view taken along lines 5b-5b in FIG. 1, and FIG. 5(c) is a cross sectional view taken along lines 5c-5c in FIG. 1.

FIG. 6 shows enlarged plan views of a relevant part of examples of the pore pattern in the top sheet or cover nonwoven sheet.

FIG. 7 is an enlarged plan view of a relevant part of an example of the pore pattern in the top sheet or cover nonwoven sheet.

FIG. 8 is a plan view illustrating an example of positioning of the moisturizer.

FIG. 9 is an explanatory schematic diagram illustrating passage of the moisturizer.

EMBODIMENTS FOR CARRYING OUT THE INVENTION

Embodiments of the present invention will now be explained in detail with reference to the attached drawings. In sectional views, a dotted pattern region represent an adhesive as joining means for joining the components on the top side and the underside of the region, and may be formed by, for example, solid, bead, curtain, summit, or spiral application, or pattern coating (transfer of a hot melt adhesive by relief printing) of a hot melt adhesive, or fixed portions of the elastic members may be formed, in place of or in addition to the above, by application of a hot melt adhesive to the external surface of the elastic members with a comb gun or a surewrap. Examples of the hot melt adhesive include, but not limited to, EVA-based, adherent rubber-based (elastomer-based), olefin-based, and polyester/polyamide-based adhesives. The joining means for joining components may alternatively be material melt-bonding, such as heat sealing or ultrasonic sealing.

Example of Tape-Type Disposable Diaper

FIGS. 1 to 5 show an example of a tape-type disposable diaper as a disposable diaper according to the present invention, wherein X refers to the overall width of the diaper except for the fastening tapes, and Y refers to the overall length of the diaper. This tape-type disposable diaper has an absorber body 56 extending from the ventral to dorsal sides, a liquid-pervious top sheet 30 covering the top side of the absorber body 56, and a liquid-impervious sheet 11 covering the underside of the absorber body 56, and has a ventral end flap EF and a dorsal end flap EF extending on the front and back sides, respectively, and not including the absorber body 56, and a pair of side flaps SF extending laterally from the opposed side edges of the absorber body 56. Each side flap SF has a narrowed portion in the middle of the front-back direction, which will fit around each leg, and a fastening tape 13 on the dorsal side of the narrowed portion.

The liquid-impervious sheet 11 is covered on its under face with a cover nonwoven sheet 20. The cover nonwoven sheet 20 extends to the peripheries of the diaper, whereas the liquid-impervious sheet 11 extends in the front-back direction up to the front and back edges of the diaper, and in the width direction up to between each side edge of the absorber body 56 and each side edge of the cover nonwoven sheet 20. However, the cover nonwoven sheet 20 may extend partially in the front-back direction, partially in the width direction, or both, as necessary. For example, when part of the liquid-impervious sheet 11 is covered with another material, such as gather nonwoven fabric, the cover nonwoven sheet 20 may not be provided over that part.

The top sheet 30 and the liquid-impervious sheet 11 in the illustrated embodiment are rectangular, and have dimensions slightly larger in the front-back and width directions than those of the absorbent element 50. The peripheral portions of the top sheet 30 extending beyond the side edges of the absorbent element 50 and the peripheral portions of the liquid-impervious sheet 11 extending beyond the side edges of the absorbent element 50 are joined, for example, with a hot melt adhesive.

The absorbent element 50 includes an absorber body 56 and a packing sheet 58 covering the absorber body 56, and may be interposed between the top sheet 30 and the liquid-impervious sheet 11, while an intermediate sheet 40 may be interposed between the top sheet 30 and the absorbent element 50.

The intermediate sheet 40 in the illustrated embodiment is shorter than the width of the absorbent element 50 and disposed in the center, but may be provided all over the width. The longitudinal dimension of the intermediate sheet 40 may be the same as the overall length of the diaper, the same as the length of the absorbent element 50, or within a small length range around the area where liquids are received. In addition, an indicator may be provided which changes color upon contact with a liquid component of the bodily waste.

On the top face of the tape-type disposable diaper on each side in the width direction, a side gather part 60 is provided. Each side gather part 60 has a first portion 61 provided on the side flap SF (planar gather portion) and a second portion 69 protruding over each side portion of the top sheet 30 (three-dimensional gather portion).

Specifically, a strip of gather nonwoven fabric 62 having the same length as the overall length Y of the diaper extends from the first portion 61 to the second portion 69. In the first portion 61, the gather nonwoven fabric strip 62 is joined to the cover nonwoven sheet 20, for example, with a hot melt adhesive, and between these nonwoven strip and sheet, one or a plurality at intervals in the width direction WD, of gathering elastic members 63 extending in the front-back direction LD are fixed in the extended state and, with the contracting force of the gathering elastic members, the first portion 61 is contracted in the front-back direction LD to form planar gathers, which will be brought into contact around each leg.

The gather nonwoven fabric strip 62 has an extending portion extending from the first portion 61 as the base toward the center of the width direction WD, and at least this extending portion is folded back in the leading edge portion to form a double-layered structure. The ends opposed in the front-back direction LD of the extending portion are fixed to the top sheet 30 to form laid-down portions 67, whereas the middle portion in the front-back direction LD located between the laid-down portions 67 forms a non-fixed, free portion 68. In the free portion 68, one or the plurality at intervals in the width direction WD, of gathering elastic members 63 extending in the front-back direction LD are fixed in the extended state and, with their contracting force, the free portion 68 of the second portion 69 is contracted in the front-back direction LD to form three-dimensional gathers, which will be brought into contact around each leg.

The fastening tape 13 in the illustrated embodiment has a base sheet forming a tape attachment portion 13C fixed to a side portion of the diaper and a tape body 13B protruding from the tape attachment portion 13C, and an engaging part 13A disposed on the tape body 13B of the base sheet in the middle of the width direction and to be engaged on the ventral side, and the portion beyond this engaging part 13A is a grip portion. The tape attachment portion 13C of the fastening tape 13 is interposed between the gather nonwoven fabric 62 as an inner layer and the cover nonwoven sheet 20 as an outer layer of the side flap, and adhered thereto with a hot melt adhesive. The engaging part 13A is joined to the inner surface of the tape body 13B with an adhesive.

The engaging part 13A may preferably be a hook member (male part) of a mechanical fastener (hook and loop fastener). The hook member has a number of engaging projections on its outer surface. The engaging projections may be (A) tick-shaped, (B) J-shaped, (C) mushroom-shaped, (D) T-shaped, (E) double J-shaped (wherein J-shaped parts are joined back to back), or the like, and may be in any of these. Needless to say, the engaging part of the fastening tape 13 may be a sticky material layer.

The base sheet forming from the tape attachment portion 13C to the tape body 13B may be of nonwoven fabric, plastic film, polyethylene-laminated nonwoven fabric, paper, or composites thereof.

For fitting the diaper on a wearer, with the dorsal side flaps SF overlapping the exterior of the ventral side flaps SF, the fastening tapes 13 are engaged in the ventral region F on the outer surface at appropriate sites. The position and the size of the sites to be engaged by the fastening tapes 13 may be decided arbitrarily.

At the sites in the ventral region F to be engaged by the fastening tapes 13, a target sheet 24 having targets for facilitating the engagement is preferably disposed. When the engaging part 13A is a hook member, the target sheet 24 may preferably be a film type having a film layer and an engaging layer provided over the outer surface of the film layer, on which engaging layer the hooks of the engaging part 13A detachably engage. In this case, the engaging layer is known to be a thread-knit web having loops, which is to be attached to the film layer, or a nonwoven layer of a thermoplastic resin, which is to be attached to the film layer through intermittent ultrasonic seals so that the fibers of the nonwoven fabric form loops. Either of these may preferably be used. Further, a filmless target tape may also be used, which is formed of embossed nonwoven fabric of a thermoplastic resin and has no film layer. On such a target tape, fastening tapes 13 engage with the hooks thereof being entangled or hooked on the loops.

When the engaging part 13A is a sticky material layer, a base sheet made of plastic film with a sticky smooth surface which has been subjected to release lining, may be used.

When the sites in the ventral region F to be engaged by the fastening tapes 13 are of nonwoven fabric, e.g., when the cover nonwoven sheet 20 in the illustrated embodiment is of nonwoven fabric, and the engaging parts 13A of the fastening tapes 13 are hook members, the target sheet 24 may be omitted, and the hook members may be caught on the nonwoven fabric of the cover nonwoven sheet 20 for engagement. In this case, the target sheet 24 may be interposed between the cover nonwoven sheet 20 and the liquid-impervious sheet 11.

The end flaps EF extend on the front and back sides of the absorbent element 50 and do not include the absorber body 56. Extending on the front side is the ventral end flap EF, and extending on the back side is the dorsal end flap EF.

The front-back dimension of the dorsal end flap EF is preferably the same as or smaller than the front-back dimension of the attachment portion of the fastening tape 13 for the reason mentioned above. If the absorbent element 50 is positioned too close to the dorsal end portion of the diaper, the thickness and stiffness of the absorbent element 50 tend to cause a gap between the dorsal end portion of the diaper and the body surface, so that the front-back dimension of the dorsal end flap EF is preferably 10 mm or larger.

The front-back dimensions of the ventral end flap EF and the dorsal end flap EF are preferably about 5 to 20% the front-back dimension Y of the overall diaper, and in baby diapers, 10 to 60 mm, particularly 20 to 50 mm.

For improved dorsal fitting of the diaper, as shown in detail in FIG. 5, an elastic member which is resiliently stretchable in the width direction, in particular, a strip-shaped dorsal stretchable sheet 70 is preferably provided between the opposed fastening tapes 13. Each end portion of the dorsal stretchable sheet 70 preferably extends to overlap the attachment portion of the corresponding fastening tape 13, but may be spaced apart from the attachment portion toward the center of the width direction. The front-back dimension of the dorsal stretchable sheet 70 is preferably about 20% larger or smaller than the front-back dimension of the attachment portion of the fastening tape 13. Further, when the dorsal stretchable sheet 70 is arranged overlapping the boundary between the dorsal end flap EF and the absorbent element 50 as illustrated, the dorsal end portion of the absorbent element 50 is pressed tightly onto the body, which is preferable.

The dorsal stretchable sheet 70 may be a sheet-shaped elastic member like a rubber sheet but, in view of air permeability, may preferably be nonwoven fabric or paper. In this case, air-permeable sheet-shaped elastic member like stretchable nonwoven fabric may be used but, as shown in FIG. 5(a), it is preferred to use two base sheets 71, such as of nonwoven fabric, bonded together with an adhesive, such as a hot melt adhesive, to fix therebetween elastic members 72 in the form of a perforated sheet, web, or elongate (thread, string, or the like) shape, or the like, in the stretched state in the width direction. The base sheet 71 here may be of a material similar to the cover nonwoven sheet 20. The elastic members 72 preferably have an elongation of about 150 to 250%. When the elastic members 72 are in an elongate shape (thread, string, or the like), it is preferred to use five to fifteen threads of the elastic members each having a fineness of 420 to 1120 dtex at 3 to 10 mm intervals.

As shown in FIG. 5(a), by arranging part of the elastic members 72 across the absorbent element 50, fitting of the absorbent element 50 is preferably improved. In this case, by causing part or all of the elastic members 72 superimposed on the absorbent element 50 to lose their contracting force, e.g., by cutting, the absorbent element 50 is kept from contracting in the width direction in its dorsal end portion, which further improves fitting.

Note that the elastic members 72 may be fixed over the entire length of the base sheets 71 along the longitudinal direction of the sheet (width direction of the diaper) but, for preventing contraction or turning-over of the sheet upon attachment to the diaper body, the contracting force may be caused to be lost or the elastic members 72 may be caused to be absent in the area of about 5 to 20 mm from each end of the sheet in the front-back direction (width direction of the diaper). In the absence of the elastic members 72, a frill out of contact with the skin may be formed, which increase air permeability.

The dorsal stretchable sheet 70, in the illustrated embodiment, is interposed between the gather nonwoven fabric 62 and the cover nonwoven sheet 20 on each lateral side of the liquid-impervious sheet 11 in the width direction, and between the liquid-impervious sheet 11 and the absorbent element 50 in the area overlapping the liquid-impervious sheet 11, but may be placed between the liquid-impervious sheet 11 and the cover nonwoven sheet 20, on the exterior surface of the cover nonwoven sheet 20, or between the top sheet 30 and the absorbent element 50.

Further, the dorsal stretchable sheet 70 may be placed on the top sheet 30 and, in this case, on the gather nonwoven fabric 62 on each lateral side of the liquid-impervious sheet 11 in the width direction. When the cover nonwoven sheet 20 is formed by stacking a plurality of base sheets, the entire dorsal stretchable sheet 70 may be interposed between the base sheets of such cover nonwoven sheet 20.

<Basic Structure of the Present Invention>

The disposable diaper according to the present invention has, referring to the explanatory reference numerals used in the above discussion of the embodiment, a top sheet 30 constituting a surface for use, a liquid-impervious sheet 11 provided on the under face side, and an absorbent element 50 interposed therebetween, wherein the top sheet 30 is of perforated nonwoven fabric having a number of holes 14 arranged at intervals and each penetrating the two sides of the fabric, and wherein a moisturizer M composed mainly of glycerin is applied to the top sheet 30.

According to the basic structure of the present invention, the top sheet 30, which is of perforated nonwoven fabric having a number of holes arranged at intervals and each penetrating the two sides of the fabric, allows smooth passage of loose stool components through its holes 14 to the absorbent element 50 having the absorber body 56, where the loose stool components are absorbed, so that not only irritation to the skin and diaper rash, caused by loose stool components remaining on the top sheet 30 surface, are suppressed, but also leakage through leg portion or back portion of the diaper may be prevented.

Further, the moisturizer M composed mainly of glycerin, which is applied to the exterior surface of the top sheet 30 (containing the moisturizer M at least in the exterior surface portion), has functions not only to protect the skin of a wearer, but also to reduce friction with the skin of a wearer.

As a result, when the disposable diaper is worn, the top sheet slides with respect to the skin in response to the posture change of a wearer to ensure contact with the skin of the wearer, which improves the leak protection effect.

The moisturizer M is provided on the top sheet 30 by application or the like manner during production of diapers, and then a quantity of diaper products is packaged compactly. This compaction of diapers causes part of the moisturizer in the top sheet 30 to pass through the holes 14 into the intermediate sheet 40, as shown schematically in FIG. 9.

Originally, the intermediate sheet has a faster body fluid permeation rate compared the top sheet 30. The moisturizer M composed mainly of glycerin has a higher hydrophilicity compared to hydrophilic diamide derivatives. As such, the moisturizer M composed mainly of glycerin, which has passed to the intermediate sheet 40, functions to draw the body fluid from the top sheet 30 side or loose stool components through the holes 14.

In this way, the body fluid from the top sheet 30 side or loose stool components through the holes 14 may be led promptly toward the absorbent element 50 side, and residence of the loose stool components or body fluid on the surface of the top sheet 30 may be controlled, which reduces skin irritation or diaper rash.

Further, the glycerin component in the moisturizer M moisturizes skin to produce a skin care effect.

In addition, the moisturizer M composed mainly of glycerin, which is applied to the exterior surface of the top sheet 30 (containing the moisturizer M at least in the exterior surface portion), functions not only to protect the skin of a wearer, but also to reduce friction with the skin of a wearer.

As a result, when the disposable diaper is worn, the top sheet slides with respect to the skin in response to the posture change of a wearer to ensure contact with the skin of the wearer, which improves the leak protection effect.

The top sheet 30 is of perforated nonwoven fabric having a number of holes 14. Though the exact reason is not known, a number of holes 14 makes smaller the area in contact with the skin of a wearer compared to nonwoven fabric without holes, to thereby exhibit function to reduce friction with the skin of the wearer. As a result, when the disposable diaper is worn, the top sheet slides with respect to the skin in response to the posture change of a wearer to ensure contact with the skin of the wearer, which improves the leak protection effect.

The shape and arrangement of the holes 14 in the top sheet 30 are not particularly limited, and the plan arrangement of the holes 14 is suitably such that imaginary lines 14$q$ connecting adjacent holes 14 form a Moroccan pattern D, as typically shown in FIG. 7.

It is preferred in view of design to arrange the holes 14 in the cover nonwoven sheet 20, if provided, in a Moroccan pattern D similar to that in the top sheet 30.

The exact reason why the Moroccan pattern D provides advantages is not clear, but it is assumed to be because the imaginary linking lines R1, R2 formed of groups of holes 14 form a rhombic lattice, and function as starting lines of deformation to facilitate deformation of the top sheet 30 (including the cover nonwoven sheet 20, if necessary) in the front-back and the width directions.

The deformation of the top sheet 30 (including the cover nonwoven sheet 20, if necessary) in the front-back and the width directions starting from the imaginary linking lines R1, R2, is followed by the easily deformable, liquid-impervious sheet 11 to cause deformation of the latter.

The moisturizer M may be applied, for example, as shown in FIG. 8, along the front-back direction at intervals in the width direction. The application may be performed, for example, by discharging the moisturizer through application nozzles disposed at intervals in the width direction in the production process, or by transferring.

For example, referring to FIG. 8, the width mx of application of the moisturizer M may be 5 to 30 mm and the length my of application in the front-back direction may be from 50 mm to the front-back length of the product, at intervals and of 5 to 30 mm.

The application in the front-back direction may be made over the front-back length of the product, but for minimizing the material cost through application focused around the crotch portion, in which the effect of the present invention is remarkable, it is preferred not to apply the moisturizer over a certain length in the front and back portion of the product.

The amount of application may preferably be 0.08 to 0.10 g/10 cm×10 cm.

With the holes 14 being arranged in the above-mentioned Moroccan pattern D and the moisturizer M being applied along the front-back direction at intervals in the width direction, the groups of holes 14 in the Moroccan pattern are arranged substantially along the width direction, as well as along the imaginary linking lines R1, R2. With such an arrangement, the applied moisturizer M may be diffused in the width and the front-back directions even to the area where the moisturizer M is not applied, so that the moisturizer M, even in a small amount, may be diffused all over.

In the embodiment, the Moroccan pattern D is formed all over the cover nonwoven sheet 20 and the top sheet 30 in the front-back direction. Formation of the Moroccan pattern D may only be in an end portion, for example, in the dorsal end portion, of a disposable diaper, but in view of difficulties in positional control of the pore formation in the cover nonwoven fabric and the top sheet material in the production process, and for securing air-permeability along the entire length, it is preferred to form the Moroccan pattern D all over the cover nonwoven sheet 20 and the top sheet 30 in the front-back direction.

The opening shape of each pore 14 may be elongate as shown in FIGS. 6(*a*) and 6(*b*), perfect circular as shown in FIGS. 6(*c*) and 6(*e*), elliptical as shown in FIG. 6(*d*), polygonal, such as triangular, rectangular, or rhombic, start shaped, cloud shaped, or any arbitrary shape.

Also in the Moroccan pattern D, the opening shape of each pore may similarly be those shown in FIG. 6.

The size of each pore 14 according to the present invention is not particularly limited and, referring to FIG. 6, the maximum dimension 14L in the front-back direction LD is preferably 0.3 to 1.8 mm, particularly 0.4 to 1.0 mm, and the maximum dimension 14W in the width direction WD is preferably 0.2 to 1.5 mm, particularly 0.3 to 1.0 mm. When the shape of each pore 14 is longer in one direction (the overall dimension in one direction is longer than the overall dimension in the direction orthogonal to that direction), such as a long hole, elliptical, rectangular, or rhombic shape, the maximum longitudinal dimension is preferably 1.2 to 2.5 times the maximum dimension in the direction orthogonal thereto. Further, when the shape of each pore 14 is longer in one direction, the longitudinal direction of the holes 14 is preferably aligned to the front-back direction LD, but may be aligned to the width direction WD or oblique.

The area of each pore 14 and the area ratio of the holes 14 may suitably be decided, and the area may preferably be about 0.1 to 2.7 mm$^2$ (particularly 0.1 to 1.0 mm$^2$) and the area ratio may preferably be about 1.0 to 15.0% (particularly 5.0 to 10.0%).

The opening shape of each pore in the Moroccan pattern may also be selected from various shapes, such as a circular shape with a diameter of 0.5 to 1.5 mm, or a shape in 0.5 to 1.5 mm size in terms of equivalent diameter, and it is preferred that the center-to-center distance between the adjacent holes is 1.0 to 4.0 mm, and the area of one non-perforated region Z encircled by the imaginary line 14$q$ connecting the holes in the Moroccan pattern is 1.0 to 3.5 cm$^2$.

The moisturizer composed mainly of glycerin according to the present invention contains, as its composition, 70 mass % or more glycerin and optionally one or a plurality of additives selected from the group consisting of emulsifiers, phosphates, paraffin, and surfactants. The surfactants may preferably be ether-type nonionic surfactants or nonionic surfactants including EO/PO surfactants.

Next, explanations will be made on the components of the embodiment.

<Cover Nonwoven Sheet>

The majority of disposable diapers and sanitary napkins are known to have structures in which an air-permeable liquid-impervious sheet is provided on the underside of an absorber body for preventing bleed-through of absorbed liquid while securing air permeability, and this liquid-impervious sheet is covered on its under face with a cover nonwoven sheet for providing fabric-like appearance and texture.

The cover nonwoven sheet 20 in the embodiment, too, is provided for giving fabric-like appearance and texture. The cover nonwoven sheet 20 covers the liquid-impervious sheet 11 on its underside, and constitutes the product external surface in at least part of the region covering the liquid-impervious sheet 11.

In this case, when an air-permeable liquid-impervious sheet is overlaid with a cover nonwoven sheet, the air-permeability is lowered by the presence of the cover nonwoven sheet. One preferred technique for solving this problem is to employ, as a cover nonwoven sheet, perforated nonwoven fabric having a number of holes penetrating the two sides of the fabric.

In the illustrated embodiment, the cover nonwoven sheet 20 is of perforated nonwoven fabric having at intervals a number of holes 14 penetrating the two sides of the fabric. The kind of fibers or the processing method in fiber bonding (interlacing) of the cover nonwoven sheet 20 is not particularly limited, and may suitably be similar to those of the exterior sheet. It is preferred to use an air-through nonwoven fabric with a preferred basis weight of 20 to 30 g/m$^2$, and a preferred thickness of 0.3 to 1.0 mm.

The cover nonwoven sheet 20 may be provided, in view of improvement in air permeability, with the holes 14 all over the front-back and the width directions, in case of tape-type disposable diapers.

(Top Sheet)

The top sheet 30 has a property to permeate liquid, and may be formed of, for example, perforated or non-perforated nonwoven fabric or porous plastic sheet. Among these, the nonwoven fabric is not particularly limited in its raw material fibers. For example, synthetic fibers, such as olefin-based including polyethylene or polypropylene, polyester-based, or polyamide-based fibers, recycled fibers, such as rayon or cupra, natural fibers, such as cotton, or mixed fibers or composite fibers of two or more of these may be used. Further, the nonwoven fabric may have been produced through any processing. The processing may include known processes, such as spunlacing, spunbonding, thermal bonding, melt-blowing, needle punching, air through, and point bonding. For example, when flexibility or draping properties are required, spunbonding or spunlacing is preferred, whereas when bulkiness or softness is required, air through, point bonding, or thermal bonding is preferred.

In particular, nonwoven fabric produced by air through method is preferred in view of bulkiness and softness.

The nonwoven fabric fibers may be, for example, of PE/PET of 1.5 to 3.5 dtex.

The basis weight of the top sheet 30 is preferably 10 to 30 g/m$^2$. At less than 10 g/m$^2$, back flow of the body liquid may occur, whereas at over 30 g/m$^2$, sufficient softness may be hard to be obtained.

The top sheet 30 may be made of one sheet, or of a laminated sheet obtained by bonding two or more sheets together. Similarly, the top sheet 30, in the planar direction, may be made of one sheet or of two or more sheets. The top sheet 30 may be folded around along the side edges of and onto the underside of the absorbent element 50, or may extend beyond the side edges of the absorbent element 50 without being folded.

The top sheet 30 is preferably fixed to the member contiguous on its underside by joining means through material melt-bonding, such as heat sealing or ultrasonic sealing, or with a hot melt adhesive, for the purpose of avoiding displacement with respect to the underside member. In the illustrated embodiment, the top sheet 30 is fixed, with the hot melt adhesive applied on its under face, to the top face of the intermediate sheet 40 and to the surface of an area of the packing sheet 58 located over the top side of the absorber body 56.

<Plan Arrangement of Holes in Top Sheet>

The top sheet 30 is of perforated nonwoven fabric having the holes 14 in order to facilitate prompt passage of body fluid to the absorbent element 50. The plan arrangement of the holes 14 may be in a regularly repeated pattern, such as a rhombic lattice pattern as shown in FIG. 6(*a*), a hexagonal lattice pattern as shown in FIG. 6(*b*) (also referred to as a staggered pattern), a square lattice pattern as shown in FIG. 6(*c*), a rectangular lattice pattern as shown in FIG. 6(*d*), a parallelogrammatic lattice pattern as shown in FIG. 6(*e*) (as illustrated, a pattern having two intersecting groups of a number of slanted parallel lines), or the like pattern (including those slanted by less than 90 degrees with respect to the front-back direction LD), as well as a pattern wherein groups of holes 14 (the arrangement in each unit group may be regular or irregular, and may be in a pattern, letter, or the like) are repeated regularly.

The distance 14$y$ in the front-back direction and the distance 14$x$ in the width direction between adjacent holes 14 in the top sheet may suitably be decided and, in view of air-permeability, preferably 14$y$ may be 0.9 to 8.0 mm and 14$x$ may be 2.0 to 10 mm, in particular, 14$y$ is 1.0 to 3.0 mm and 14$x$ is 3.0 to 5.0 mm. In particular, as shown in FIG. 6(*d*), it is preferred that lines of holes 14 arranged in the front-back direction at front-back intervals 14$y$ smaller than the front-back dimension 14L of each pore 14 are repeated at predetermined intervals in the width direction WD, with the interval 14$x$ in the width direction being larger than the front-back dimension 14L of each pore 14 (more preferably, three times or more the dimension 14W of each pore 14 in the width direction), which leads to significant increase in air permeability without losing softness and bulkiness, and without decrease in tensile strength of the sheet in the front-back direction, which is important during production, and thus is preferred. In this case, it is particularly preferred that the shape of each pore 14 is elongate in the front-back direction LD.

Of course, in bonding the top sheet 30 and the intermediate sheet 40, thermal adhesion or ultrasonic adhesion may be used, but hot melt adhesion is preferred for securing softness.

(Intermediate Sheet)

For promptly passing the liquid penetrating the top sheet 30 to the absorber body, an intermediate sheet (also referred to as a second sheet) 40 may be provided, of which liquid permeation rate is faster than that of the top sheet 30. This intermediate sheet 40 is capable not only of promptly passing liquid to the absorber body to increase absorption performance by the absorber body, but also preventing "back flow" phenomenon of the absorbed liquid back from the absorber body to keep the top sheet 30 surface always dry. The intermediate sheet 40 may be omitted.

The intermediate sheet 40 may be of the materials similar to those for the top sheet 30, or spunlaced, spunbonded, SMS, or pulp nonwoven fabric, pulp-rayon composite sheets, point-bonded fabric, or crepe paper. In particular, air through nonwoven fabric is preferred for its bulkiness. For air through nonwoven fabric, composite fibers of core-shell structure are preferably used, wherein the resin for the core may be polypropylene (PP), or preferably polyester (PET), which is highly rigid. The basis weight is preferably 20 to 80 $g/m^2$, more preferably 25 to 60 $g/m^2$. The fineness of the raw material fibers of the nonwoven fabric is preferably 2.0 to 10 dtex. For making nonwoven fabric bulky, it is also preferred to use eccentric fibers having off-centered cores, hollow fibers, or eccentric hollow fibers, entirely as the raw material fibers or partially mixed fibers.

In the illustrated embodiment, the width of the intermediate sheet 40 is shorter than the width of the absorber body 56 and arranged in center, but may be provided over the entire width. The longitudinal dimension of the intermediate sheet 40 may be the same as the entire length of the diaper, the same as the length of the absorbent element 50, or within a short length around the liquid receiving area.

The intermediate sheet 40 is preferably fixed to the member contiguous on its underside by joining means through material melt-bonding, such as heat sealing or ultrasonic sealing, or with a hot melt adhesive, for the purpose of avoiding displacement with respect to the underside member. In the illustrated embodiment, the intermediate sheet 40 is fixed, with the hot melt adhesive applied on its under face, to the surface of that area of the packing sheet 58 which is located over the top side of the absorber body 56.

(Liquid Impervious Sheet)

Materials of the liquid-impervious sheet 11 is not particularly limited, and may be, for example, plastic film made of olefin-based resins or the like, such as polyethylene or polypropylene, laminated nonwoven fabric wherein plastic film is laminated over nonwoven fabric, or a laminated sheet wherein nonwoven fabric or the like is laid over and joined on plastic film. The liquid-impervious sheet 11 may be made of a material which is preferably used for preventing dampness and is not liquid-pervious and is moisture-permeable. As moisture-permeable plastic film, microporous plastic film is widely used, which is obtained by kneading an inorganic filler in an olefin-based resin, such as polyethylene or polypropylene, molding the resulting mixture into a sheet, and then uni- or biaxially drawing the sheet. Also, nonwoven fabric of microdenier fibers, or sheets that have been rendered liquid-impervious without using plastic film through a process, such as enhancement of leak proof property by applying heat or pressure to minimize interfiber gaps, or coating with a highly water-absorbable resin or a hydrophobic resin or water repellent, may be used as the liquid-impervious sheet 11. For sufficient bonding strength in bonding to a cover nonwoven sheet 20 via a hot melt adhesive as will be discussed later, use of plastic film is preferred.

The liquid-impervious sheet 11 may have a width to fit behind the absorbent element 50 as illustrated, or may be folded around along both side edges of the absorbent element 50 to extend to the opposed sides of the top sheet 30. The width of such extensions may suitably be about 5 to 20 mm on each opposed side.

Inside of the liquid-impervious sheet 11, in particular on the side faces of the absorber body 56, an excretion indicator which changes in color upon absorption of a liquid component, may be provided.

(Side Gather Part)

Each side gather part 60 extends all over the front-back direction LD, and is provided to be brought into contact around each leg of a wearer to prevent side leakage. Those generally referred to as three-dimensional gathers 69 and planar gathers 61 fall under this part.

The gather nonwoven fabric 62 may preferably be flexible nonwoven fabric having excellent uniformity and concealability, such as spunbonded nonwoven fabric (SS, SSS, or the like), SMS nonwoven fabric (SMS, SSMMS, or the like), or melt-blown nonwoven fabric, which may have been subjected to water-repellent treatment with silicone or the like, as required. The basis weight of the fibers may preferably be about 10 to 30 $g/m^2$. The elongate elastic members 63 may be of rubber thread or the like. When spandex rubber thread is used, the fineness is preferably 470 to 1240 dtex, more preferably 620 to 940 dtex. The stretch rate in the fixed state is preferably 150 to 350%, more preferably 200 to 300%. Note that the term "stretch rate" refers to a value with respect to the natural length being 100%. Further, as illustrated, a waterproof film may be interposed between duplicate gather nonwoven fabric 62. In this case, the gather nonwoven fabric 62 may partially be omitted in the area where the waterproof film is present, but in order to impart fabric-like appearance and texture to the product, the exterior of each side gather part 60 at least from its root end to its leading edge is required to be formed of the gather nonwoven fabric 62, as in the illustrated embodiment.

The number of the elongate elastic members 63 provided in the free section of each side gather part 60 is preferably 2 to 6, more preferably 3 to 5.

(Absorbent Element)

The absorbent element 50 includes the absorber body 56 and the packing sheet 58 packing the entire absorber body 56.

(Absorber Body)

The absorber body 56 may be formed of an assembly of fibers. Such an assembly of fibers may be an accumulation of short fibers of fluff pulp, synthetic fibers, or the like, as well as an assembly of filaments obtained by opening, where necessary, a tow (fiber bundle) of synthetic fibers, such as cellulose acetate. The basis weight of the fibers may be about 100 to 300 $g/m^2$ for an accumulation of fluff pulp or short fibers, and about 30 to 120 g/m² for an assembly of filaments. The fineness of the synthetic fibers, when used, is, for example, 1 to 16 dtex, preferably 1 to 10 dtex, more preferably 1 to 5 dtex. In an assembly of filaments, the filaments may be of uncrimped fibers, but crimped fibers are preferred. The number of crimps of the crimped fibers may be, for example, 5 to 75, preferably 10 to 50, more preferably 15 to 50 per inch. Uniformly crimped fibers are often used. In the absorber body 56, superabsorbent polymer particles are preferably dispersed and retained.

The absorber body 56 may be in a rectangular shape, or in the shape of an hourglass having the front end, the back end, and a narrowed section located between the front and back ends and having a narrower width compared to the front and back ends.

The size of the absorber body 56 may suitably be decided as long as the absorber body extends to the front, back, left, and right of the position of the urination port.

(Superabsorbent Polymer Particles)

The absorber body 56 may be caused partially or entirely to contain superabsorbent polymer particles. The superabsorbent polymer particles include not only "particles", but also "powders". The superabsorbent polymer particles may be those used in this type of disposable diapers as they are, and may preferably be particles 30 wt % or less of which, after sieving (five-minute shaking), remain on a 500 μm standard sieve (JIS Z8801-1: 2006) and particles 60 wt % or more of which, after sieving (five-minute shaking), remain on a 180 μm standard sieve (JIS Z8801-1: 2006).

Any material of the superabsorbent polymer particles may be used without particular limitation, and those having a water absorption of 40 g/g or more are preferred. The superabsorbent polymer particles may be of starch-based, cellulose-based, or synthetic polymer-based. Starch-acrylic acid (salt) graft copolymers, saponified products of starch-acrylonitrile copolymers, cross-linked sodium carboxymethyl cellulose, or acrylic acid (salt) polymers may be used. The superabsorbent polymer particles may preferably be in ordinary powder or granular form, but particles in other forms may also be used.

The superabsorbent polymer particles having a water absorption rate of 70 seconds or less, particularly 40 seconds or less, may preferably be used. With too slow a water absorption rate, so-called back flow may likely to occur, wherein liquid supplied into the absorber body 56 returns out of the absorber body 56.

The superabsorbent polymer particles may preferably be those having a gel strength of 1000 Pa or higher. With such property, when the superabsorbent polymer particles are formed into a bulky absorber body 56, stickiness after liquid absorption may effectively be limited.

The basis weight of the superabsorbent polymer particles may suitably be decided depending on the absorption amount required in a use of the absorber body 56. Thus, it depends, but the basis weight may be 50 to 350 g/m². At a basis weight of the polymer less than 50 g/m², the absorption amount may hardly be secured. At over 350 g/m², the effect may be saturated.

Where necessary, the spread density or spread amount of the superabsorbent polymer particles may be adjusted in the horizontal direction of the absorber body 56. For example, the spread amount on the liquid excretion area may be larger than that on the remaining areas. Considering the sexual difference, the spread density (amount) on the front side may be higher for men's, whereas the spread density (amount) in the center portion may be higher for women's. Further, the absorber body 56 in its horizontal direction may be provided with a local (e.g., spot) area without the polymer.

(Packing Sheet)

For limiting escape of the superabsorbent polymer particles, or for improving maintenance of the shape of the absorber body 56, the absorber body 56 is wrapped with a packing sheet 58.

The material of the packing sheet 58, when used, may be tissues, in particular, crepe paper, nonwoven fabric, polyethylene-laminated nonwoven fabric, perforated sheet, or the like.

Conventionally, crepe paper is often used. In the present invention, SMS nonwoven fabric (spunbonded/melt-blown/spunbonded laminated nonwoven fabric) or SMMS nonwoven fabric (spunbonded/melt-blown/melt-blown/spunbonded laminated nonwoven fabric) is used.

With crepe paper, in which pulp fibers extend in the front-back direction (MD) and arranged densely, rigidity particularly in the front-back direction is high (with less softness).

In contrast, with SMS or SMMS nonwoven fabric, for example, rigidity particularly in the front-back direction is low (with excellent softness), and bending rigidity in the front-back direction (MD) and in the 45-degree oblique direction is lower, compared to those with crepe paper, as will be shown by the results of cantilever test.

As a result, the disposable diaper, when worn, deforms well (bends well) in response to the posture change of the wearer and is securely brought into contact with the skin of the wearer, which leads to improved leak protection.

The materials of the SMS nonwoven fabric or SMMS nonwoven fabric may be polypropylene, polyethylene/polypropylene composite material, or the like. In particular, nonwoven fabric subjected to hydrophilization treatment for improving body fluid absorption characteristics is preferred.

The materials having a basis weight of preferably 5 to 40 g/m², particularly 10 to 30 g/m² are preferred.

How to pack with the packing sheet 58 may suitably be decided and, in view of readiness of production or protection against leakage of the superabsorbent polymer particles through the front or back end edge, preferably the packing sheet 58 is wrapped cylindrically around the absorber body 56 to surround its top and under faces as well as both side faces, with the front and back edge portions of the packing sheet extending forwardly and backwardly beyond the absorber body 56, and the overlaid wrapping portion as well as the overlapped portions in the front and back extensions are joined with joining means, such as a hot melt adhesive or material melt-bonding.

Where needed, the absorber body 56 may be covered only on its top and under faces with two separate sheets of nonwoven fabric, with both side faces being uncovered.

<Explanation of Terms in the Specification>

The following terms appearing in the present specification shall have the following meaning unless otherwise specified herein.

The "front-back (longitudinal) direction" refers to the direction connecting the ventral side (front side) and the dorsal side (back side), whereas the "width direction" refers to the direction orthogonal to the front-back direction (right-left direction).

The "top side" refers to the side of a tape-type disposable diaper, when worn, closer to the skin of the wearer, whereas the "underside" refers to the side of a tape-type disposable diaper, when worn, away from the skin of the wearer.

The "top face" refers to the face of a tape-type disposable diaper, when worn, closer to the skin of the wearer, whereas the "under face" refers to the face of a tape-type disposable diaper, when worn, away from the skin of the wearer.

The "area ratio" refers to the ratio of the objective area per unit area, and is represented in percentage by dividing the sum of the areas of objective portions (e.g., holes) in an objective region (e.g., cover nonwoven sheet) by the area of that objective region. In a configuration where a number of objective portions are provided at intervals, the area ratio is preferably determined with the objective region being set to a size containing 10 or more objective portions. For example, the area ratio of the holes may be determined in the following procedure, using, for example, VHX-1000 (tradename) manufactured by KEYENCE under the measurement conditions in ×200 magnification.

(1) Place a specimen under a ×20 magnification lens, and adjust the focus. Position the nonwoven fabric so that 4×6 holes are in the field.
(2) Specify the brightness of the pore portions, and measure the area of the holes.
(3) Click the color extraction in "Area Measurement" under "Measurement and Comment". Click the pore portions.
(4) Click "Collective Measurement", check "Display the measurement result window", and store in CSV data.

The "stretch rate" refers to a value with respect to the natural length being 100%.

The "gel strength" is determined as follows. To 49.0 g of artificial urine (a mixture of 2 wt % urea, 0.8 wt % sodium chloride, 0.03 wt % calcium chloride dihydrate, 0.08 wt % magnesium sulfate heptahydrate, and 97.09 wt % ion-exchanged water), 1.0 g of superabsorbent polymer is added and stirred with a stirrer. The resulting gel is left in a chamber with constant temperature and humidity at 40° C. at 60% RH for 3 hours, and then the temperature is returned to the ordinary temperature. The gel strength is measured in a curd meter (Curd-meter-MAX ME-500 manufactured by I. techno Engineering).

The "basis weight" is determined as follows. A specimen or test piece is preliminarily dried, left in a laboratory or in apparatus under the standard conditions (20±5° C. temperature and 65% or lower relative humidity in the testing location) until constant mass is attained. The preliminary drying means attaining constant mass from a specimen or test piece in the environment not exceeding a relative humidity of 10 to 25% and a temperature of 50° C. No preliminary drying may be performed on fibers with an official regain of 0.0%. From the test piece of the constant mass, a specimen of 200 mm×250 mm size (±2 mm) is cut out, using a plate of 1 g/m² (200 mm×250 mm, ±2 mm). The weight of the specimen is measured and multiplied by 20 times to calculate the weight per 1 m², which is taken as the basis weight.

The "thickness" is automatically measured using an automatic thickness meter (KES-G5 handy compression tester program) under a load of 10 gf/cm² with the compression area of 2 cm².

The water absorption is determined in accordance with JIS K7223-1996 "Testing method for water absorption capacity of super absorbent polymers".

The water absorption rate is defined as the "time spent until the end point is reached" in carrying out JIS K7224-1996 "Testing method for water absorption rate of super absorbent polymers" using 2 g of superabsorbent polymer and 50 g of saline.

The "spread state" refers to the state in which an article is spread flatly without contraction or slack.

The size of each part refers to the size not in the natural length state but in the spread state, unless otherwise specified.

Unless the environmental conditions of a test or measurement are otherwise specified, the test or measurement shall be conducted in a laboratory or in apparatus under the standard conditions (20±5° C. temperature and 65% or lower relative humidity in the testing location).

Next, Examples and Comparative Examples are disclosed to demonstrate the effects of the present invention.
<Prototype>

EXAMPLE 1

A tape-type disposable diaper of a structure as shown in FIGS. 1 to 5 was produced using, as the top sheet 30, air-through nonwoven fabric which was prepared by air through method using fiber material of PE/PET=50/50 in 2.5 dtex and had a basis weight of 20 g/m². The top sheet had holes arranged in the Moroccan pattern having dimensions as shown in FIG. 7 as follows:
Diameter of circular pore 14: 1.0 mm
14$px$, 14$py$=2.5 mm
14X=16 mm
14Y=18 mm On this top sheet, a moisturizer M containing 80 mass % or more glycerin was applied in the amount of 0.085 g/10 cm×10 cm in the width of application mx being 5 mm and the front-back length of application being 140 mm, at 5 mm intervals md, as shown in FIG. 8, to thereby obtain a disposable diaper of Example 1.

Comparative Example 1

A disposable diaper of Comparative Example 1 was obtained in the same way, except that a top sheet without holes was used, and the moisturizer M was not applied.

Comparative Example 2

A disposable diaper of Comparative Example 2 was obtained in the same way, except that the moisturizer M was applied to a top sheet without holes.

Comparative Example 3

A disposable diaper of Comparative Example 3 was obtained in the same way, except that the moisturizer M was not applied.

These disposable diapers were subjected to a loose stool permeation test. Specifically, an absorption test was performed, wherein a disposable diaper was placed in its spread state, a cylinder of 7 cm diameter was disposed on the top sheet side, and 1 ml of an artificial loose stool was introduced. After the lapse of 30 minutes following the introduction of the artificial loose stool, each disposable diaper was disassembled, a measurement area of 10 cm×10 cm was cut out, weight increment of the top sheet and of the intermediate sheet were respectively calculated, and the difference was taken as the weight increment of the absorber body.

As the artificial loose stool, a known yogurt-type artificial loose stool was used. Here, the artificial loose stool contained 2 parts of commercially available yogurt and 3 parts of ion exchanged water by mass, and was prepared to have a viscosity of 4.5 mPa·s.

The results are shown in Table 1.

TABLE 1

|  | Example 1 | Comp. Example 1 | Comp. Example 2 | Comp. Example 3 |
|---|---|---|---|---|
| Pores in top sheet | Present | Absent | Absent | Present |
| Presence/ Absence of moisturizer | Present | Absent | Present | Absent |
| Kind of moisturizer | Glycerin | None | Glycerin | None |
| Amount of loose stool (g) | | | | |
| Top sheet | 0.503 | 0.568 | 0.526 | 0.545 |
| Intermediate sheet | 0.057 | 0.054 | 0.041 | 0.055 |
| Absorber body | 0.440 | 0.378 | 0.433 | 0.400 |

The results revealed that with the diaper of Example 1, the loose stool remaining on the top sheet was in a small amount, and was definitely caused to pass to the absorber body, and thus is capable of providing good suppression of diaper rash.

INDUSTRIAL APPLICABILITY

The present invention may be applied to disposable diapers in general, including not only tape-type disposable diapers, but also pad-type disposable diapers and underpants-type disposable diapers.

DESCRIPTION OF REFERENCE NUMERALS 11 liquid-impervious sheet
20 cover nonwoven sheet
20H hot melt adhesive
14 pore
30 top sheet
40 intermediate sheet
50 absorbent element
56 absorber body
58 packing sheet
60 side gather part
62 gather nonwoven fabric
LD front-back direction
WD width direction

The invention claimed is:

1. A disposable diaper comprising a top sheet constituting a surface for use, a liquid-impervious sheet provided on an under face side, and an absorbent element interposed therebetween,
    wherein an intermediate sheet, which has a faster body fluid permeation rate compared to the top sheet, is interposed between the top sheet and the absorbent element,
    wherein the top sheet is formed of a first air through nonwoven fabric having a basis weight of 10 to 30 g/m$^2$, and wherein the first air through nonwoven fabric is perforated having a number of holes arranged at intervals and each penetrating two sides of the fabric,
    wherein the intermediate sheet is formed of a second air through nonwoven fabric having a basis weight of 20 to 80 g/m$^2$, and a fineness of raw material fibers of the second air through nonwoven fabric is 2.0 to 10 dtex,
    wherein imaginary linking lines connecting groups of the holes form a Moroccan pattern with a rhombic lattice which is slanted with respect to a front-back direction and a width direction all over the top sheet,
    wherein an area of one non-perforated region encircled by an imaginary line connecting the holes in the Moroccan pattern with a rhombic lattice is 1.0 to 3.5 cm$^2$,
    wherein each of the holes is in a circular shape with a diameter of 0.5 to 1.5 mm or a shape in 0.5 to 1.5 mm size in terms of equivalent diameter, and a center-to-center distance between adjacent holes in the front-back direction and the width direction is 1.0 to 4.0 mm, and
    wherein a hydrophilic moisturizer containing 80 mass % or more glycerin is applied to the top sheet.

2. The disposable diaper according to claim 1, wherein the moisturizer is applied along the front-back direction at intervals in the width direction.

* * * * *